United States Patent
Sivasubramanian et al.

(10) Patent No.: US 9,901,912 B2
(45) Date of Patent: Feb. 27, 2018

(54) SUPER ACIDS AND BASES AS DEHYDROCONDENSATION CATALYSTS

(71) Applicant: Momentive Performance Materials Inc., Waterford, NY (US)

(72) Inventors: Karthikeyan Sivasubramanian, Bangalore (IN); Vivek P. Khare, Bangalore (IN)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 15/169,941

(22) Filed: Jun. 1, 2016

(65) Prior Publication Data

US 2016/0354769 A1    Dec. 8, 2016

Related U.S. Application Data

(60) Provisional application No. 62/169,788, filed on Jun. 2, 2015.

(51) Int. Cl.
| | | |
|---|---|---|
| *C08G 77/08* | (2006.01) | |
| *C08G 77/38* | (2006.01) | |
| *B01J 31/02* | (2006.01) | |
| *C07F 7/18* | (2006.01) | |
| *C08L 83/04* | (2006.01) | |

(52) U.S. Cl.
CPC ....... *B01J 31/0275* (2013.01); *B01J 31/0222* (2013.01); *B01J 31/0225* (2013.01); *B01J 31/0227* (2013.01); *B01J 31/0241* (2013.01); *B01J 31/0264* (2013.01); *B01J 31/0271* (2013.01); *C07F 7/188* (2013.01); *C08G 77/08* (2013.01); *C08G 77/38* (2013.01); *C08L 83/04* (2013.01); *B01J 2231/40* (2013.01)

(58) Field of Classification Search
None
See application file for complete search history.

(56) References Cited

U.S. PATENT DOCUMENTS

| | | | |
|---|---|---|---|
| 4,515,620 A | * | 5/1985 | Bohner .................. A01N 47/34 504/178 |
| 6,875,880 B2 | | 4/2005 | Nishiwaki et al. |
| 7,605,284 B2 | | 10/2009 | Brueckner et al. |
| 7,825,209 B2 | | 11/2010 | Knott et al. |
| 8,217,122 B2 | | 7/2012 | Morita et al. |
| 8,455,562 B2 | | 6/2013 | Maliverney |
| 8,470,899 B2 | | 6/2013 | Maliverney |
| 8,470,951 B2 | | 6/2013 | Maliverney |
| 9,006,357 B2 | | 4/2015 | Yang et al. |
| 2001/0047070 A1 | | 11/2001 | Priou et al. |
| 2005/0136269 A1 | | 6/2005 | Doehler et al. |
| 2006/0041097 A1 | | 2/2006 | Herrwerth et al. |

FOREIGN PATENT DOCUMENTS

| | | |
|---|---|---|
| DE | 765551 | 1/1957 |
| DE | 102004001407 A1 | 7/2005 |
| JP | 11-061010 | 3/1999 |
| WO | 2012/104346 A1 | 8/2012 |

OTHER PUBLICATIONS

Written Opinion and International Search Report from PCT/US2016/035165 dated Jul. 21, 2016.

* cited by examiner

*Primary Examiner* — Zinna Northington Davis
(74) *Attorney, Agent, or Firm* — James C. Abruzzo

(57) ABSTRACT

There is provided herein a composition which contains hydride-functionalized siloxane or silane, a hydroxyl-containing compound that does not contain silicon, and a catalytically-effective amount of super acid or super base catalyst selected from the group consisting of a triaza-containing compound which contains only carbon, nitrogen and hydrogen atoms, an atrane compound, a linear or branched compound containing a sulfonyl group and a fluoro group, and combinations thereof. There is also provided a process of making such a composition.

18 Claims, No Drawings

SUPER ACIDS AND BASES AS DEHYDROCONDENSATION CATALYSTS

This application claims priority to Provisional U.S. Patent Application No. 62/169,788 filed on Jun. 2, 2015, the entire contents of which are incorporated herein by reference in their entirety.

FIELD OF THE INVENTION

This invention is directed to the use of acids and bases as catalysts. More particularly, the invention provides compositions, containing one or more of various specific super acids and bases and their use in a specific type of reaction. There are also provided specific applications which contain such compositions such as agrochemical, personal care, home care and coatings.

BACKGROUND OF THE INVENTION

Synthesizing Si—O—C bonds via reaction between a hydride functionalized siloxane and a material containing an OH group, particularly an alcohol, known as a dehydrocondensation reaction, has been used to synthesize a variety of functionalized siloxanes. These siloxanes can find applicability in numerous applications such as agrochemical, personal care, home care and coatings.

However, conventional siloxanes prepared using traditional dehydrocondensation reactions can be ineffective for producing curable polysiloxane compositions in the absence of certain condensation catalysts, for example tin-based catalysts, and/or in the substantial absence of moisture. Accordingly, there is a need for improved siloxane compositions that overcome these disadvantages.

SUMMARY OF THE INVENTION

It has now been discovered that specific variants of Si—H and R—OH dehydrocondensation reactions have significant catalytic selectivity and/or activity by using the specific super acid or base catalysts described herein.

In accordance with the present invention, there is provided a composition comprising:

(A) a hydride-functionalized siloxane or silane, (B) a hydroxyl-containing compound that does not contain silicon, and (C) a catalytically-effective amount of super acid or super base catalyst selected from the group consisting of a triaza-containing compound which contains only carbon, nitrogen and hydrogen atoms, an atrane compound, a linear or branched compound containing a sulfonyl group and a fluoro group, and combinations thereof.

There is also provided herein in another embodiment a process which comprises: reacting components (A) and (B) described above, in the presence of (C) as described above.

DETAILED DESCRIPTION OF THE INVENTION

The present invention relates to a composition which contains a silyl-hydride containing component and an alcohol moiety containing material that does not contain silicon and a dehydrocondensation reaction of these components in the presence of specific super acid or base catalysts. These compositions, when reacted, produce silicone products containing at least one Si—O—C bond, which can be incorporated into numerous applications, such as the non-limiting examples of an agrochemical composition, a personal care application, such as those intended for application to skin or hair, a home care application such as a laundry detergent or fabric softener, or a hard surface cleaner and a coating application, such as the non-limiting example of a waterborne coating.

Other than in the working examples or where otherwise indicated, all numbers expressing amounts of materials, reaction conditions, time durations, quantified properties of materials, and so forth, stated in the specification and claims are to be understood as being modified in all instances by the term "about" whether or not the term "about" is used in the expression.

It will be understood that any numerical range recited herein includes all sub-ranges within that range and any combination of the various endpoints of such ranges or sub-ranges, be it described in the examples or anywhere else in the specification.

It will also be understood herein that any of the components of the invention herein as they are described by any specific genus or species detailed in the examples section of the specification, can be used in one embodiment to define an alternative respective definition of any endpoint of a range elsewhere described in the specification with regard to that component, and can thus, in one non-limiting embodiment, be used to supplant such a range endpoint, elsewhere described.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof. Thus, for example, the term "catalyst" as used herein shall be understood to refer to individual or single catalyst components or substances as well as mixtures thereof.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

As used herein, the term "hetero" refers to the presence of at least one heteroatom, such as O, N, S and the like.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

As used herein "consisting essentially of" in terms of the composition, contains the hydride-functional siloxane or silane (A), hydroxyl-containing compound that does not contain silicone (B), and catalytically-effective amount of super acid or super base catalyst (C) described herein, as well as optionally any one of an agrochemical component, a personal care component, a home care component, or a coating component.

As used herein "consisting of" in terms of the in terms of the composition, contains the hydride-functionalized siloxane or silane (A), hydroxyl-containing compound that does not contain silicone (B), and catalytically-effective amount of super acid or super base catalyst (C) described herein.

As used herein, the term "super acid" refers to an acid having acidity greater than that of 100% sulfuric acid, as determined using means generally known in the art. In particular, super acids may be characterized as acids having a Hammett acidity function ($H_0$) that is less (i.e., more negative) than that of 100% sulfuric acid, which has an ($H_0$) of −12. These acids, and other super acids, may be obtained commercially, for example, from Sigma-Aldrich. Additionally, or alternatively, the super acids may optionally be formed in situ using means generally known in the art.

The expression "super base" as used herein is understood to be an extremely basic compound or substance that has a high affinity for protons; defined semi-quantitatively a super base can be any species with a higher absolute proton affinity (APA=245.3 kcal/mol) and intrinsic gas phase basicity (GB=239 kcal/mol) than Alder's canonical proton sponge (1,8-bis-(dimethylamino)-naphthalene).

Polysiloxanes suitable for use as hydride-functionalized siloxane component (A) of the composition of the invention includes polyorganosiloxanes, fluorinated polyorganosiloxanes, and combinations thereof (preferably, polyorganosiloxanes; more preferably, polyalkyl(hydro)siloxanes) comprising reactive silane functionality comprising at least one, preferably at least two hydrosilyl moieties (that is, monovalent moieties comprising a hydrogen atom bonded directly to a silicon atom). The polysiloxanes/silanes can be small molecules, oligomers, polymers, or a combination thereof. Preferably, the polysiloxanes/silanes are polymers. The polysiloxanes/silanes can be linear, branched, or cyclic. Useful polymers include those that have random, alternating, block, or graft structures, or a combination thereof.

The molecular weight and the reactive hydride functionality of component (A) (including the number and nature of the hydride moieties) can vary widely, depending upon, for example, the molecular weight and the specific hydroxyl-containing component (B) and the properties desired for the composition. The silanes/polysiloxanes (A) preferably have a weight average molecular weight of about 100 to about 100,000, more specifically from about 200 to about 80,000 and most specifically from about 200 to about 6,000.

A preferred class of polysiloxanes that are suitable as component (A) includes those that can be represented by the following general formula (I):

$$R'_2R''SiO(R'_2SiO)_r(HR'SiO)_sSiR''R'_2 \quad (I)$$

wherein R' is independently selected from alkyl, alkenyl, fluoroalkyl, aryl, fluoroaryl, cycloalkyl, fluorocylcloalkyl, heteroalkyl, heterofluoroalkyl, heteroaryl, heterofluoroaryl, heterocycloalkyl, heterofluorocycloalkyl and combinations thereof containing from 1 to about 60 carbon atoms, preferably up to about 30 carbon atoms and most preferably up to about 12 carbon atoms, preferably, each R' is independently selected from alkyl (preferably, having 1 to about 8 carbon atoms), fluoroalkyl (preferably, having 3 to about 8 carbon atoms; more preferably, $R^fC_2H_4$—, wherein $R^f$ is a fluorinated or perfluorinated alkyl group having 1 to about 6 carbon atoms (preferably, 1 to about 6 carbon atoms)), aryl, and combinations thereof (with alkyl being most preferred). More preferably, each R' is independently selected from methyl, $C_4F_9C_2H_4$—, $C_6F_{13}C_2H_4$—, $CF_3C_2H_4$—, phenyl, $C_6H_5C_2H_4$—, and combinations thereof (even more preferably, methyl, $CF_3C_2H_4$—, phenyl, $C_4F_9C_2H_4$—, and combinations thereof; most preferably, methyl); each R" is independently hydrogen (hydro) or R'; r is an integer of 0 to about 150 (preferably, 0 to about 100; more preferably, 0 to about 20); and s is an integer of 1 to about 150 (preferably, about 1 to about 100; more preferably, about 1 to about 50). Most preferably, both R" and R' are methyl, r is 0, and/or s is one.

Preferred hydride-functional polysiloxanes include those comprising polymethyl(hydro)siloxane homopolymer, as well as those comprising copolymer(s) comprising methyl (hydro)siloxane units and up to about 40 or 50 mole percent of other units selected from dialkylsiloxane units, (alkyl) (methyl)siloxane units, and (alkyl)(phenyl)siloxane units wherein each alkyl group is independently selected from alkyl groups having 1 to about 8 carbon atoms (for example, hexyl), di(fluoroalkyl)siloxane units, (fluoroalkyl)(methyl) siloxane units, and (fluoroalkyl)(phenyl)siloxane units wherein each fluoroalkyl group is independently selected from fluoroalkyl groups having 3 to about 8 carbon atoms (for example, trifluoropropyl or nonafluorohexyl), diphenyl-siloxane units, and combinations thereof. Although homopolymer is often preferred, copolymers can be preferred for some applications.

The polysiloxanes/silanes useful as component (A) can be used in the composition of the invention, preferably in a curable composition, singly or in the form of mixtures of different polysiloxanes. The polysiloxanes/silanes can be prepared by known synthetic methods and many are commercially available.

In one embodiment herein the hydroxyl-containing compound which does not contain silicon (B) includes linear, branched or cyclic alcohols, diols, polyols, glycols and the like. In one embodiment, the component (B) contains at least one hydroxyl moiety, preferably at least two hydroxyl moieties and can contain up to about 6 hydroxyl moieties.

Preferably the component (B) is of the general formula R—OH wherein R is an organic group containing from 1 to about 20 carbon atoms, more specifically from 1 to about 12 carbon atoms and most specifically from 1 to about 6 carbon atoms. In one embodiment, the organic group of R is any of an alkyl, alkene, aryl, cycloalkyl, heteroalkyl, heteroaryl, and heterocycloalkyl, and combinations thereof containing from 1 to about 60 carbon atoms, preferably up to about 30 carbon atoms and most preferably up to about 12 carbon atoms, preferably, each R is independently selected from alkyl (preferably, having 1 to about 8 carbon atoms), heterocycloalkyl, and combinations thereof (with heterocycloalkyl being most preferred). More preferably, each R is independently selected from methyl, phenyl, $C_6H_5C_2H_4$—, furfuryl, tetrahydrofurfuryl, most preferably tetrahydrofurfuryl.

In one embodiment component (B) is an alcohol selected from the group consisting of furfuryl alcohol, tetrahydrofurfuryl alcohol, amyl alcohol, benzyl alcohol, cyclohexanedimethanol, diacetone alcohol, hexyl alcohol, 1,2-hexanediol, butylene glycol, diethylene glycol, dipropylene glycol, ethyl hexanediol, ethylene glycol, hexylene glycol, pentylene glycol, propylene glycol, tetraethylene glycol, triethylene glycol, or tripropylene glycol; polyethylene glycol, butanetriol, glycerol, 1,2,6-hexanetriol, alkoxylated alcohol including laureth-12, ceteareth-20, laureth-23, glycereth-7, glycereth-12, glycereth-26, PEG-4, PEG-6, PEG-8, PEG-12, PEG-32, PEG-75, PEG-150, trimethylolpropane, trimethylolethane, trimethylolmethane, 2-hydroxymethyl-1, 6-hexanediol, 2-hydroxymethyl-1,4-butanediol, 2-hydroxymethyl-1,5-pentanediol and combinations thereof.

The amount of hydroxyl moieties in component (B) can be chosen to comport with the amount of hydride moieties present in component (A) as described herein, i.e., to be present in an about an equimolar amount. In one non-limiting embodiment herein the molar ratio of hydride groups in component (A) to hydroxyl groups in component (B) is in a range of from about 0.1/1 to about 1.9/1, more specifically in a range of from about 0.5/1 to about 1.5/1, and most specifically in a range of from about 0.9/1 to about 1.1/1.

Catalysts which are suitable as super acid or super base catalyst (C) can be those as described herein, more specifically, those selected from the group consisting of a triaza-containing compound which contains only carbon, nitrogen and hydrogen atoms, an atrane compound, a linear or branched compound containing a sulfonyl group and a fluoro group, and combinations thereof.

The triaza-containing compound which contains only carbon, nitrogen and hydrogen atoms which can function as the super acid or super base catalyst (C) can preferably be a triazabicyclo-containing compound, such as triazabicyclo-containing compounds wherein each of the cyclic structures in the bicyclic moiety contain from 2 to about 7 carbon atoms, more specifically from 2 to about 5 carbon atoms and most specifically 3 carbon atoms. In one embodiment, one of the cyclic moieties in the bicyclic structure can have a different cyclic structure from the other cyclic moiety, and in some embodiments, they can have the same cyclic structure. In a preferred embodiment, both of the cyclic moieties in the bicyclic structure have the same structure of having 3 carbon atoms. As is understood in the art, the expression "triaza" indicates the replacement of 3 carbon atoms in a structure with 3 nitrogen atoms.

In a further embodiment herein the triazabicyclo-containing compound which contains only carbon, nitrogen and hydrogen atoms is a triazabicycloalkene containing at least one C=N bond. As is understood in the art, the nomenclature of a specific aza-cyclic-alkene-containing compound is such that the nomenclature of the alkene reflects the total number of carbon and nitrogen atoms in the overall cyclic structure, such as for example herein, wherein the triazabicycloalkene which contains only carbon, nitrogen and hydrogen atoms described herein is such that it contains from 3 to about 15 carbon atoms, preferably from 4 to about 12 and most preferably from 5 to about 8 carbon atoms. In one non-limiting embodiment herein the triazabicycloalkene which contains only carbon, nitrogen and hydrogen atoms contains 6 carbon atoms.

One non-limiting example of the triaza-containing compound described herein can be 1,5,7-triazabicyclo[4,4,0] decene.

The atrane compound described herein as the super acid or super base catalyst (C) can be any atrane compound, such as for example, atrane, quasitrane and protrane compounds. Examples of suitable atrane compounds include silatrane, boratrane, phosphatranes. In one non-limiting embodiment the atrane compound can contain from 6 to about 30 carbon atoms, more specifically from 6 to about 24 carbon atoms and most specifically from 6 to about 20 carbon atoms. In one embodiment the atrane compound contains 18 carbon atoms. In one embodiment the atrane compound is a phosphatrane, more specifically an azaphosphatranc compound, even more specifically an alkylazaphosphatrane compound wherein the alkyl moiety contains from 1 to about 6 carbon atoms.

In one embodiment the alkylazaphosphatrane is a trialkylazaphosphatrane, wherein each of the alkyl moieties independently contains from 1 to about 6 carbon atoms, more specifically from 1 to about 4 carbon atoms, such as the non-limiting examples of methyl, ethyl, propyl, isopropyl, butyl, isobutyl, sec-buty and tert-butyl, most preferably isobutyl.

The linear or branched compound containing a sulfonyl group and a fluoro group described herein as the super acid or super base catalyst (C) can be selected from a compound containing a sulfonic acid group and a fluoro group, a compound containing a sulfonate group and a fluoro group, a compound containing a sulfonimide group and a fluoro group, and combinations of such compounds.

In one embodiment herein the compound containing a sulfonic acid group and a fluoro group is a fluorinated alkane sulfonic acid wherein the fluorinated alkane moiety contains from 1 to about 6 carbon atoms, more specifically from 1 to about 4 carbon atoms, most specifically about 4 carbon atoms. Some suitable examples of the fluorinated alkane sulfonic acid compound are trifluoromethanesulfonic acid, pentafluoroethanesulfonic acid, heptafluoropropanesulfonic acid, nonafluorobutanesulfonic acid, undecafluoropentanesulfonic acid, tridecafluorohexanesulfonic acid, pentadecafluoroheptasulfonic acid, heptadecafluorooctanesulfonic acid, nonadecafluorononanesulfonic acid and combinations thereof.

In another embodiment, the compound containing a sulfonate group and a fluoro group further comprises an organosilyl group wherein the organo group contains from 1 to about 4 carbon atoms, more specifically from 1 to 3 carbon atoms. In some embodiments the compound containing a sulfonate group and a fluoro group further comprises triorganosilyl group wherein each organo group independently contains from 1 to about 4 carbon atoms, preferably from 1 to 3 carbon atoms and more preferably 1 carbon atoms, e.g., methyl. In one embodiment, the triorganosilyl group is a trimethylsilyl group. Some suitable examples of organo groups present in the compound containing a sulfonate group and a fluoro group further comprising an organosilyl group (or a triorganosilyl group) independently are selected from alkyl, alkenyl, aryl, cycloalkyl, heteroalkyl, heteroaryl, heterocycloalkyl, and combinations of groups thereof each containing from 1 to about 60 carbon atoms, preferably up to about 30 carbon atoms, more preferably up to about 12 carbon atoms, and most preferably from 1 to about 6 carbon atoms, such as the non-limiting example of methyl.

The fluoro group in the compound containing a sulfonate group and a fluoro group can be a fluoroalkane group containing from 1 to 3 carbon atoms, more specifically such as trifluoropropyl, trifluoroethyl, trifluoromethyl and the like.

In one non-limiting example the compound containing a sulfonate group and a fluoro group is selected from the group consisting of trimethylsilyltrifluoromethanesulfonic acid, trimethylsilylpentafluoroethanesulfonic acid, trimethylsilylheptafluoropropanesulfonic acid, trimethylsilylnonafluorobutanesulfonic acid, trimethylsilylundecafluoropentanesulfonic acid, trimethylsilyltridecafluorohexanesulfonic acid, trimethylsilylpentadecafluoroheptasulfonic acid, trimethylsilylheptadecafluorooctanesulfonic acid, trimethylsilylnonadecafluorononanesulfonic acid and combinations thereof.

In one other embodiment, the compound containing a sulfonimide group and a fluoro group is a bis(fluoroalkyl) sulfonimide compound wherein the fluoroalkyl group contains from 1 to about 3 carbon atoms, more specifically such as trifluoropropyl, trifluoroethyl, trifluoromethyl and the like. For example, the compound containing a sulfonimide group and a fluoro group can be selected from the group consisting of bis(trifluoromethane)sulfonimide, bis(pentafluoroethane)sulfonimide, bis(heptafluoropropane)sulfonimide, bis(nonafluorobutane) sulfonimide, bis(undecafluoropentane)sulfonimide, bis(tridecafluorohexane)sulfonimide, bis(pentadecafluoroheptae)sulfonimide, bis(heptadecafluorooctane)sulfonimide, bis(nonadecafluorononane)sulfonimide and combinations thereof.

In yet another embodiment, bis(fluoroalkyl)sulfonimide compound can further comprise a triorganosilyl moiety. Some examples of the organo moiety present in the triorganosilyl moiety are the same as the organo moieties described above for the organo groups present in the compound containing a sulfonate group and a fluoro group further comprising an organosilyl group (or a triorganosilyl group).

In one non-limiting embodiment the bis(fluoroalkyl)sulfonimide compound further comprising a triorganosilyl moiety can be selected from the group consisting of N-trimethylsilylbis(trifluoromethane)sulfonimide, N-trimethylsilylbis(pentafluoroethane)sulfonimide, N-trimethylsilylbis(heptafluoropropane)sulfonimide, N-trimethylsilylbis(nonafluorobutane) sulfonimide, N-trimethylsilylbis(undecafluoropentane)sulfonimide, bis(tridecafluorohexane)sulfonimide, N-trimethylsilylbis(pentadecafluoroheptae)sulfonimide, N-trimethylsilylbis(heptadecafluorooctane)sulfonimide, N-trimethylsilylbis(nonadecafluorononane)sulfonimide and combinations thereof.

In one specific embodiment, the super acid or super based catalyst is selected from the group consisting of 1,5,7-tiazabicyclo[4,4,0]decene; triisobutylazaphosphatrane; perfluorobutanesulfonic acid; trimethylsilyltrifluoromethaneslufonate; bis(trifluoromethane)sulfonimide; N-trimethylsilylbis(trifluoromethane)sulfonimide; and, combinations thereof.

The catalytically-effective amount of a sulfonyl-containing super acid or super base catalyst (C) can vary widely depending on the specific reactants and the specific catalyst chosen. Some non-limiting examples of catalytically-effective amounts of catalyst (C) that can be present are from about 0.1 wt % to about 2.0 wt %, more specifically, from about 0.3 wt % to about 1.5 wt % and most specifically from about 0.3 wt % to about 1.3 wt %, said weight percents being based on the total weight of the composition.

Apart from the effectiveness of the catalyst for catalyzing the reaction of interest, the catalyst might also play a role in changing the distribution of the products formed. Depending on the catalyst (super acid or a super base) a particular distribution of product might be formed. The difference in the product distribution is evident from Table 1.

In one non-limiting embodiment, this particular distribution of product that may be formed by using the catalyst described herein would favor the production of a siloxane molecule containing an Si—O—C bond such as is formed by the hydrocondensation of the hydrogen atom in an alcohol component (B) described herein, and the hydrogen atom in the hydride-functionalized siloxane component (A) described herein, as opposed to the production of less desirable byproducts such as those formed from the cleaving of the Si—O—Si bond in the component (A), which cleaved silicone unit thereof, is then bound to the residue of the alcohol component to form an Si—O—C bond but wherein less than the full silicone chain of initial component (A) is present; and, also wherein a cleaved silicone unit bonds to another molecule of the siloxane (A) at the site of the displaced hydrogen atom.

Minor amounts of optional components can be added to the composition to impart particular desired properties for particular curing methods or uses. Useful compositions can comprise conventional additives such as, for example, other catalysts than those described herein, (including conventional condensation catalysts such as tin catalysts, which can be added as co-catalysts if desired), initiators, emulsifiers (including surfactants), stabilizers, anti-oxidants, flame retardants, adhesion promoters (for example, trialkoxysilanes), release modifiers (for example, silicate MQ resin), colorants, thickeners (for example, carboxy methyl cellulose (CMC), polyvinylacrylamide, polypropylene oxide, polyethylene oxide/polypropylene oxide copolymers, polyalkenols), water scavengers, and the like, and mixtures thereof.

In surprising contrast with prior art compositions, the composition(s) described herein can be effective in a curable polysiloxane composition in the substantial absence of other condensation catalysts and/or in the substantial absence of moisture. The compositions herein can be tin-free, curable polysiloxane compositions, without the need for changes in the nature of the polysiloxane components of conventional tin-cured polysiloxane compositions.

In one other embodiment there is provided herein a catalytic dehydrocondensation process comprising reacting components (A) and (B) described above, in the presence of (C) as described above. In one embodiment, the process described herein produces the composition described herein.

The step of reacting can comprise combining components (A), (B), and (C) in essentially any order (preferably, with agitation or stirring). Preferably, components (A) and (B) are combined initially, followed by addition of component (C) (preferably, as a pre-formed catalyst composition). The curable composition can be maintained as a relatively shelf-stable, 2-part system (for example, by keeping component (C) separate from the other two components), if desired, but a 1-part system (comprising all three components) can also be stable for periods of up to, for example, about several days in dry solvent (a relatively long pot life), prior to application of the composition.

The step of reacting can be conducted at temperatures of from about −20° C. to about 200° C., preferably from about 15° C. to about 80° C. and most preferably from about 25°

C. to about 60° C. The time period of the reacting step can comprise from about 20 minutes to about 12 hours, more preferably from about 1 hour to about 10 hours and most preferably from about 4 hours to about 8 hours.

The composition of the invention can be cured to provide crosslinked networks having properties that can be tailored to the requirements of various different applications (for example, by varying the natures, relative amounts, and/or degrees of reactive functionality of starting components (A) and/or (B)).

The relative amounts of components (A) and (B) can vary widely, depending upon their nature and the desired properties of the curable and/or cured composition. Although stoichiometry prescribes a 1:1 molar ratio of reactive silane functionality (for example, one mole of hydrosilyl moieties for every mole of alcohol moieties), in practice it can be useful to have a deficiency or an excess of hydrosilyl functionality (for example, this can be useful when cure inhibitors are present). Molar ratios (of hydrosilyl moieties to alcohol moieties) up to, for example, about 8:1 or about 13:1 or even as high as about 35:1 can be useful.

In one non-limiting embodiment herein, there is provided a functionalized siloxane containing a Si—O—C bond, which bond was formed by the dehydro condensation process described herein.

In one embodiment herein the composition herein can be added to an agrochemical composition for use in agrochemical applications such as pesticides.

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

The pesticidal compositions of the present invention also include at least one pesticide, where the organomodified silylated surfactant of the present invention is present at an amount sufficient to deliver between 0.005% and 2% to the final use concentration, either as a concentrate or diluted in a tank mix. Optionally the pesticidal composition may include excipients, cosurfactants, solvents, foam control agents, deposition aids, drift retardants, micronutrients, fertilizers and the like. The term pesticide means any compound used to destroy pests, e.g., rodenticides, insecticides, miticides, fungicides, and herbicides.

Buffers, preservatives and other standard excipients known in the art also may be included in the agrochemical composition.

Solvents may also be included in the agrochemical compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2, 2, 4-trimethyl, 1-3-pentane diol and alkoxylated (especially ethoxylated) versions thereof or N-methyl-pyrrilidone.

Moreover, cosurfactants, can be added to the agrochemical composition. The cosurfactants useful herein include nonionic, cationic, anionic, amphoteric, zwitterionic, polymeric surfactants, or any mixture thereof. Surfactants are typically hydrocarbon based, silicone based or fluorocarbon based.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates, and their derivatives; amine alkoxylates, especially amine ethoxylates; fatty acid alkoxylates; fatty alcohol alkoxylates; alkyl sulfonates, alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

In a preferred embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo) and Quest (Helena Chemical, Collierville, Tenn.), modified clays such as Surround® (Englehard Corp.,), foam control agents, surfactants, wetting agents, dispersants, emulsifiers, deposition aids, antidrift components, and water.

Suitable agrochemical compositions are made by combining, in a manner known in the art, such as by mixing, one or more of the above components with the organomodified silylated surfactant of the present invention, either as a tank-mix, or as an "in-can" formulation. The term "tank-mix" means the addition of at least one agrochemical to a spray medium, such as water or oil, at the point of use. The term "in-can" refers to a formulation or concentrate containing at least one agrochemical component. The "in-can" formulation may then diluted to use concentration at the point of use, typically in a tank-mix, or it may be used undiluted.

In one embodiment herein, the composition described herein can be added to a personal care formulation for use in a personal care application for skin and/or hair. Some such non-limiting examples of personal care applications are selected from the group consisting of deodorants, antiperspirants, antiperspirant/deodorants, shaving products, skin lotions, moisturizers, toners, bath products, cleansing products, shampoos, conditioners, mousses, styling gels, hair sprays, hair dyes, hair color products, hair bleaches, waving products, hair straighteners, nail polish, nail polish remover, nail creams and lotions, cuticle softeners, sunscreen, insect repellent and anti-aging products, lipsticks, foundations, face powders, eye liners, eye shadows, blushes, makeup, pet grooming products, and mascaras.

In a preferred embodiment of the present invention, cosmetic components known in the art may be incorporated in the personal care formulation for improving skin appearance. These components can be any of anti-blotching, anti-aging, eye contour, slimming, soothing/sunburn, anti-irritating, skin firming and lifting, free radical scavengers, hydratives, vitamins and anti-oxidants and minerals. Amounts of any of these aforementioned personal care formulation materials may range anywhere from 0.0001 to 5% by weight of the personal care formulation.

In one embodiment herein there is provided a home care formulation comprising the composition (i.e. of (A), (B) and (C)) described herein. Home care formulations can include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dishwashing detergents and sheeting agents, carpet cleaners, prewash spotters, rust cleaners and scale removers.

In one other embodiment herein there is provided a coating formulation comprising the composition (i.e. of (A), (B) and (C)) described herein. Typically, coatings formulations will require a wetting agent or surfactant for the purpose of emulsification, compatibilization of components, leveling, flow and reduction of surface defects. Additionally, these additives may provide improvements in the cured or dry film, such as improved abrasion resistance, antiblocking, hydrophilic and hydrophobic properties. Coating formulations may exist as solvent-borne coatings, water-borne coatings and powder coatings.

The coatings components may be employed as architecture coatings, OEM product coatings such as automotive coatings and coil coatings, special purpose coatings such as industrial maintenance coatings and marine coatings. Typical synthetic resin types for coatings substrates include polyesters, polyurethanes, polycarbonates, acrylics and epoxies.

EXAMPLES

The following examples exemplify, but do not limit, the present invention.

The structures of the catalysts used herein are provided in Figure 1. Super Acids, super bases and bicyclic guanidine base were used: 1,5,7 Triazabicyclo[4,4,0]decene (1), Tri-isobutyl-Azaphosphatrane (2), Perfluorobutanesulfonic acid (3a), Trimethylsilyltrifluoromethanesulfonate (3b), Bis(trifluoromethane)sulfonimide (4a), N-trimethylsilylbis(trifluoromethane)sulfonimide (4b).

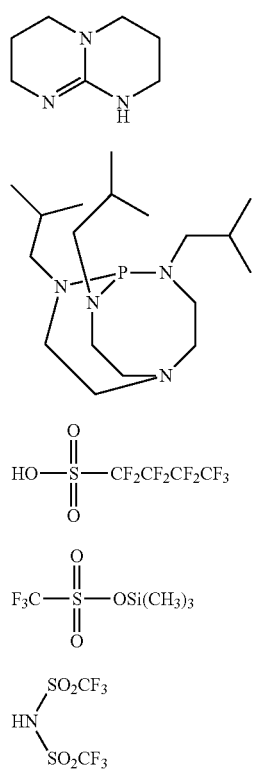

(1)

(2)

(3a)

(3b)

(4a)

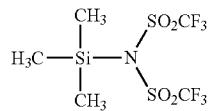

(4b)

The dehydrocondensation reaction between hydride functionalized silane/siloxane and tetrahydrofurfuryl alcohol was performed with the catalysts (1-6) at a catalyst loading ranging from 0.6 wt % to 1.3 wt %. The catalyst was added as a neat liquid or as a solid. In a typical reaction, 1 gm (0.0045 mol) of MD$^H$M and 0.459 gm (0.0045 mol) of the tetrahydrofurfuryl alcohol was taken along with the required quantity of the catalyst and the mixture was heated to 50° C. for 6 h (Scheme 1). The results are tabulated in Table 1.

The results presented in Table 1 clearly indicate that product distribution obtained depends on the type of catalyst (super acid or super base). All the catalysts used are effective for dehydrocondensation reaction. The super base type catalysts provided much better selectivity towards the product of interest as compared to the super acid catalyst as shown in Table 1. Apart from the product of interest (heptamethyltetrahydrofurfuryloxy trisiloxane) (7a), the catalysts also lead to the formation of Trimethyltetrahydrofurfuryloxy silane (7b) and methyl tris(trimethylsiloxy)silane (7c). The acid/base type catalysts are known for its ability to cleave Si—O—Si bonds. The formation of products 7b and 7c could be attributed to the fact that acid/base type catalysts are known for its ability to cleave siloxane bonds. Interestingly with the acid type catalysts (3 and 4), we see the presence of unreacted tetrahydrofurfuryl alcohol (6) whereas with the base type catalysts (1 and 2), both the starting materials (5 and 6) are consumed.

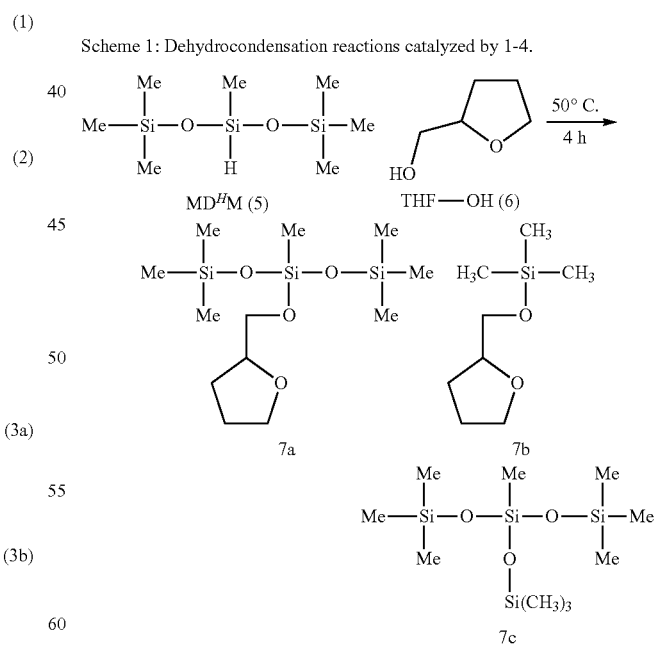

Scheme 1: Dehydrocondensation reactions catalyzed by 1-4.

Example 1

To 1 gm (4.50 mmol) of MD$^H$M and 0.459 gm (4.50 mmol) of tetrahydrofurfurylalcohol, 20 mg of the catalyst (Triazabicyclo[440]undecene (1)) was added and the reaction was conducted at 50 C for 6 h. After 6 h, the reaction mixture was analyzed by GC-MS to determine the product composition. GC-MS analysis indicated the formation of the dehydrocondensation product. The results are provided in Table 1.

Example 2

To 1 gm (4.50 mmol) of $MD^HM$ and 0.459 gm (4.50 mmol) of tetrahydrofurfurylalcohol, 20 mg of the catalyst (Triisobutyl-Azaphosphatrane (2)) was added and the reaction was conducted at 50 C for 6 h. After 6 h, the reaction mixture was analyzed by GC-MS to determine the product composition and the formation of dehydrocondensed product. GC-MS analysis indicated the formation of the dehydrocondensation product. The results are provided in Table 1. The product distribution presented here are area percentage.

Example 3

To 1 gm (4.5 mmol) of $MD^HM$ and 0.459 gm (4.50 mmol) of tetrahydrofurfurylalcohol, 20 mg of the catalyst (Perfluorobutanesulfonicacid (3a)) was added and the reaction was conducted at 50 C for 6 h. After 6 h, the reaction mixture was analyzed by GC-MS to determine the product composition. GC-MS analysis indicated the formation of the dehydrocondensation product. The results are provided in Table 1.

Example 4

To 1 gm (4.50 mmol) of $MD^HM$ and 0.459 gm (4.50 mmol) of tetrahydrofurfurylalcohol, 20 mg of the catalyst (Trimethylsilyltrifluoromethanesulfonate (3b)) was added and the reaction was conducted at 50 C for 6 h. After 6 h, the reaction mixture was analyzed by GC-MS to determine the product composition. GC-MS analysis indicated the formation of the dehydrocondensation product. The results are provided in Table 1.

Example 5

To 1 gm (4.50 mmol) of $MD^HM$ and 0.459 gm (4.50 mmol) of tetrahydrofurfurylalcohol, 20 mg of the catalyst (Bis(trifluoromethane)sulfonimide (4a)) was added and the reaction was conducted at 50 C for 6 h. After 6 h, the reaction mixture was analyzed by GC-MS to determine the product composition. GC-MS analysis indicated the formation of the dehydrocondensation product. The results are provided in Table 1.

Example 6

To 1 gm (4.50 mmol) of $MD^HM$ and 0.459 gm (4.50 mmol) of tetrahydrofurfurylalcohol, 20 mg of the catalyst (N-trimethylsilylbis(trifluoromethane)sulfonimide (4b)) was added and the reaction was conducted at 50 C for 6 h. After 6 h, the reaction mixture was analyzed by GC-MS to determine the product composition. GC-MS analysis indicated the formation of the dehydrocondensation product. The results are provided in Table 1.

TABLE 1

Product distribution obtained with various catalysts (1-4) (nd—not dectected). The product distribution presented here are area percentage.

| | (5) | (6) | (7a) | (7b) | (7c) |
|---|---|---|---|---|---|
| 1 | nd | 1.93 | 33.3 | 7.42 | 26.01 |
| 2 | nd | 0.74 | 20.1 | 24.3 | 15.9 |
| 3a | nd | 44.07 | 0.34 | 40.60 | 0.82 |
| 3b | 0.53 | 27.2 | 2.41 | 11.4 | 13.7 |
| 4a | 8.27 | 43.7 | nd | 17.2 | 0.76 |
| 4b | 6.61 | 60.7 | nd | 5.18 | 1.03 |

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention but that the invention will include all embodiments falling within the scope of the appended claims.

The invention claimed is:
1. A composition comprising:
   (A) a hydride-functionalized siloxane or silane,
   (B) a hydroxyl-containing compound that does not contain silicon, and
   (C) a catalytically-effective amount of a super acid or super base catalyst selected from the group consisting of (1) a triazabicyclo-containing compound, (2) azaphosphatrane-containing compound, (3) a linear or branched compound selected from the group consisting of a compound containing sulfonic acid group and a fluoro group, a compound containing a sulfonate group and a fluoro group, a compound containing a sulfonimide group and a fluoro group, and combinations thereof.

2. The composition of claim 1 wherein the hydroxyl-containing compound that does not contain silicone is of the formula R—OH wherein R is an organic group containing from 1 to about 20 carbon atoms.

3. The composition of claim 1 wherein the triazabicyclo-containing compound is a triazabicycloalkene containing from 3 to 15 carbon atoms.

4. The composition, of claim 1 wherein the triazabicyclo-containing compound is a triazabicycloalkene containing from 4 to 12 carbon atoms.

5. The composition of claim 1 wherein the triazabicyclo-containing compound is a triazabicycloalkene containing from 5 to 8 carbon atoms.

6. The composition of claim 1 wherein the azaphosphatrane-containing compound is an alkylazaphosphatrane wherein the alkyl group contains from 1 to 6 carbon atoms.

7. The composition of claim 1 wherein the compound containing a sulfonic acid group and a fluoro group is a fluorinated alkane sultbnic acid wherein the fluorinated alkane group contains from 1 to 6 carbon atoms.

8. The composition of claim 1 wherein the compound containing a sulfonic acid group and a fluoro group is a fluorinated alkane sulfonic acid selected from the group consisting of trifluoromethanesulfonic acid, pentafluorobutanesulfonic acid, heptafluoropropanesulfonic acid, nonafluorobutanesultunic acid, undecafluoropentanesulfonic acid, tridecafluorohexanesulfonic acid, pentadecafluoroheptasulfonic acid, heptadecafluorooctanesulfonic acid, nonadecafluorononanesulfonic acid and combinations thereof.

9. The composition of claim 1 wherein the compound containing a sulfonate group and fluoro group further comprises an organosilyl group wherein the organo group contains from 1 to 4 carbon atoms and wherein the fluoro group is a fluoroalkane group containing from 1 to 3 carbon atoms.

10. The composition of claim 1 wherein the compound containing a sulfonate group and fluoro group further comprises an organosilyl group and is selected from the group consisting of trimethylsilyltrifluoromethanesulfonic acid, trimethylsilylpentafluoroethanesulfonic acid, trimethylsilylheptafluoropropanesulfonic acid, trimethylsilylundecafluorobutanesulfonic acid, trimethylsilylundecafluoropentanesulfonic acid, trimethylsilyltridecafluorohexanesulfonic acid, trimethylsilylpentadecafluoroheptasulfonic acid, trimethylsilylheptadecafluorooctanesulfonic acid, trimethylsilylnonadecafluorononanesulfonic acid and combinations thereof.

11. The composition of claim 1 wherein the compound containing a sulfonimide group and fluoro group is a bis(fluoroalkyl) sulfonimide compound wherein the fluoroalkyl group contains from 1 to 3 carbon atoms.

12. The composition of claim 1 wherein the compound containing a sulfonimide group and fluoro group is a bis(fluoroalkyl)sulfonimide compound selected from the group consisting of bis(trifluoromethane)sulfonimmide, bis(pentafluoroethane)sulfonimide, bis(heptafluompropane)sulfonimide, bis(nonafluorobutane) sulfonimide, bis(undecafluoropentane)sulfonimide, bis(tridecafluorohexane)sulfonimide, bis(pentadecafluoroheptae)sulfonimide, bis(heptadecafluorooctane)sulfonimide, bis(nonadecafluorononane)sulfonimide and combinations thereof.

13. The composition of claim 11 wherein the bis(fluoroalkyl)sulfonimide compound further comprises a triorganosilyl moiety.

14. The composition of claim 13 wherein the bis(fluoroalkyl)sulfonimide compound further comprising a triorganosilyl moiety is selected from the group consisting of N-trimethylsilylbis(trifluoromethane)sulfonimide,N-trimethylsilyibis(pentafluoroethane)sulfonimide, N-trimethylsilylbis(heptafluoropropane)sulfonimide, N-trimethylsilyibis(nonafluorobutane) sulfonimide, N-trimethylsilybis(undecafluoropentane)sulfonimide, bis(tridecafluorohexane)sulfonimide,N-trimethylsilyibis(pentadecafluoroheptae)sulfonimide, N-trimethylsilylbis(heptadecafluorooctane)sulfonimide, N-trimethylsilylbis(nonadecafluorononane)sulfonimide and combinations thereof.

15. The composition of claim 1 wherein the catalytically-effective amount of a sulfonyl-containing super acid or a super base catalyst is from about 0.5 wt % to about 1.5 wt % based on the total weight of the composition.

16. A catalytic dehydrocondensation process comprising: reacting the composition of claim 1.

17. The functionalized siloxane containing a Si—O—C bond formed by the process of claim 16.

18. A formulation which is an agrochemical formulation, a personal care formulation, a personal care formulation or a coating formulation which comprises the functionalized siloxane of claim 17.

* * * * *